United States Patent
Perez Golf et al.

(10) Patent No.: US 10,308,577 B2
(45) Date of Patent: *Jun. 4, 2019

(54) PROCESS FOR THE SEPARATION OF GLYCOLS

(71) Applicant: SHELL OIL COMPANY, Houston, TX (US)

(72) Inventors: Carmelo Perez Golf, Amsterdam (NL); Evert Van Der Heide, Amsterdam (NL); Pieter Huizenga, Amsterdam (NL); Kai Jurgen Fischer, Amsterdam (NL)

(73) Assignee: SHELL OIL COMPANY, Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/761,616

(22) PCT Filed: Sep. 21, 2016

(86) PCT No.: PCT/EP2016/072465
§ 371 (c)(1),
(2) Date: Mar. 20, 2018

(87) PCT Pub. No.: WO2017/050847
PCT Pub. Date: Mar. 30, 2017

(65) Prior Publication Data
US 2019/0062244 A1    Feb. 28, 2019

(30) Foreign Application Priority Data

Sep. 23, 2015  (EP) ..................... 15186563
May 23, 2016  (EP) ..................... 16170910

(51) Int. Cl.
*C07C 29/80*  (2006.01)
*C07C 29/84*  (2006.01)

(52) U.S. Cl.
CPC .............. *C07C 29/80* (2013.01); *C07C 29/84* (2013.01)

(58) Field of Classification Search
None
See application file for complete search history.

(56) References Cited

U.S. PATENT DOCUMENTS

| 4,966,658 A | 10/1990 | Berg |
| 5,423,955 A | 6/1995 | Berg |
| 2011/0312050 A1 | 12/2011 | Zhang et al. |
| 2012/0184783 A1 | 7/2012 | Barnicki |

FOREIGN PATENT DOCUMENTS

| CN | 102372600 A | 3/2012 |
| CN | 102643165 A | 8/2012 |
| WO | 2015150520 A1 | 10/2015 |

OTHER PUBLICATIONS

U.S. Appl. No. 15/533,815, filed Jun. 7, 2017.*
International Search Report and Written Opinion received for PCT Patent Application No. PCT/EP2016/072465, dated Dec. 19, 2016, 8 pages.
International Search Report and Written Opinion received for PCT Patent Application No. PCT/EP2017/062153, dated Aug. 28, 2017, 8 pages.

* cited by examiner

*Primary Examiner* — Rosalynd A Keys

(57) ABSTRACT

A process for the production of high purity mono-ethylene glycol (MEG) from a product stream of a saccharide hydrogenolysis process. The process having the steps of: (i) removing solvent from the product stream to provide a solvent-lean product stream; (ii) subjecting the solvent-lean product stream to distillation to provide a bottoms stream comprising high boiling by-products and a top stream comprising a mixture comprising MEG and 1,2-butanediol (1,2-BDO); (iii) providing said mixture having MEG and 1,2-BDO as a feed to a distillation column; (iv) providing a feed comprising an extractant of C3 to C6 alcohols and mixtures thereof to the distillation column above the mixture comprising MEG and 1,2-BDO; (v) removing a stream comprising MEG and the extractant as a bottoms stream from the distillation column; and (vi) subjecting the stream comprising MEG and the extractant to distillation to provide a top stream comprising high purity MEG.

14 Claims, 2 Drawing Sheets

PROCESS FOR THE SEPARATION OF GLYCOLS

PRIORITY CLAIM

The present application is the National Stage (§ 371) of International Application No. PCT/EP2016/072465, filed 21 Sep. 2016, which claims priority from European Application Nos. 15186563.1, filed 23 Sep. 2015 and 16170910.0, filed 23 May 2016 incorporated herein by reference.

FIELD OF THE INVENTION

The present invention relates to a process for the selective separation of glycols.

BACKGROUND OF THE INVENTION

Glycols and in particular ethylene glycol and propylene glycol are valuable materials with a multitude of commercial applications, e.g. as heat transfer media, antifreeze, and precursors to polymers, such as PET. Most glycols are prepared by industrial routes from petrochemicals derived from crude oil. For example, ethylene and propylene glycols are typically made on an industrial scale by hydrolysis of the corresponding alkylene oxides, which are the oxidation products of ethylene and propylene, produced from fossil fuels.

In recent years, increased efforts have focused on producing chemicals, including glycols, from renewable feedstocks, such as sugar-based materials. For example, US20110312050 describes a continuous process for the catalytic generation of polyols from cellulose, in which the cellulose is contacted with hydrogen, water and a catalyst to generate an effluent stream comprising at least one polyol. CN102643165 is directed to a catalytic process for reacting saccharides in an aqueous solution with hydrogen in the presence of a catalyst in order to generate polyols.

As with many chemical processes, the reaction product stream in these reactions comprises a number of desired materials, diluents, by-products and other undesirable materials. In order to provide a high value process, the desirable product or products must be obtainable from the reaction product stream in high purity with a high percentage recovery of each product and with as low as possible use of energy and complex equipment.

In known processes to make glycols, the glycols are usually present at high dilution in a solvent, typically water. The water is usually removed from the glycols by distillation. Subsequent purification of the glycols is then carried out by fractional distillation. This process can have high costs both in terms of capital and operational expenditure. Further, repeated heating or maintenance at raised temperatures in the fractional distillation steps may also lead to decomposition of the desired glycol products.

When glycols are produced by hydrogenolysis of saccharides, a mixture of diols, including glycols and other by-products is produced. The main glycol constituents in the reaction product stream are monoethylene glycol (MEG), monopropylene glycol (MPG) and 1,2-butanediol (1,2-BDO). Other diols, such as 2,3-butanediol (2,3-BDO), pentanediols, hexanediols and heptanediols may also be present. The separation of these diols by fractional distillation is complicated due to the similarity in boiling points. For example, MEG and 1,2-BDO have normal boiling points of 198 and 196.8° C., respectively. Further, the isolation of a pure MEG overheads stream by fractional distillation from a mixture comprising MEG and 1,2-BDO is made impossible by the formation of a homogeneous minimum boiling azeotrope between MEG and 1,2-BDO at atmospheric pressure. A similar close-boiling, azeotrope-forming glycol pair is MPG and 2,3-pentanediol. Other close boiling and/or azeotropic mixtures may also be formed between other diols present, further complicating the purification process.

Degradation of the products at high temperatures makes the use of higher than atmospheric pressure for distillation undesirable.

Methods to separate diols and, in particular, 1,2-BDO and MEG have been described in the art.

U.S. Pat. No. 4,966,658 is directed to the separation of a mixture of 1,2-BDO and MEG using a process known as azeotropic distillation in which an azeotrope-forming agent is added to the mixture before distillation in order to facilitate separation. Suitable azeotrope-forming agents are stated to include 3-heptanone, o-xylene, cumene and heptane. A similar process is described in U.S. Pat. No. 5,423,955 for the separation of 1,2-BDO and MPG, in this case using (among others) toluene, o-xylene, cumene and heptane as azeotrope-forming agents. Azeotropic distillation can lead to an increase in relative volatility between the components but also leads to further process steps in order to remove the azeotrope forming agents.

CN102372600 describes an extractive distillation process for the separation of glycols. In this process, a mixture of MEG, MPG and 1,2-BDO are fed to a distillation column and contacted therein with an extractant. The top product, comprising the light extractant and 1,2-BDO, is then separated in a further distillation column. The bottom product, comprising MEG, MPG and extractant is subjected to further distillation to provide MEG as the bottoms product. Suitable extractants are stated to include C6-C9 aromatics, alkanes, alkenes, C6-C11 ketones or ethers with toluene, o-xylene, cumener, n-heptane, n-octane, 3-heptanone and diethylene glycol dimethyl ether mentioned as preferred extractant. This teaching appears to be somewhat inconsistent with the above cited cases, which name the materials as azeotrope-forming agents.

WO2015150520 discloses a process for separating monoethylene glycol from a mixture comprising monoethylene glycol and 1,2-butanediol, using a two column, pressure-swing distillation set-up.

It would be advantageous to provide a simple and efficient method suitable for the recovery of desired diol products, such as MEG or MPG, from a mixture of diols from a product stream derived from a saccharide hydrolysis process or other bio-based processes.

SUMMARY OF THE INVENTION

Accordingly, the present invention provides a process for the production of a high purity first diol, selected from the group consisting of C2 to C7 diols from a product stream comprising two or more C2 to C7 diols, said process comprising the steps of:
(i) subjecting the product stream to distillation in a first distillation column to provide a bottoms stream comprising high boiling by-products and a top stream comprising a mixture comprising the two or more C2 to C7 diols;
(ii) providing said mixture comprising the two or more C2 to C7 diols as a feed to a second distillation column;
(iii) providing a feed comprising an extractant to the second distillation column above the mixture comprising the two or more C2 to C7 diols;

(iv) operating the second distillation column at a temperature in the range of from 50 to 250° C. and a pressure in the range of from 0.1 to 400 kPa;

(v) removing a stream comprising the first diol and the extractant as a bottoms stream from the second distillation column; and (vi) subjecting the stream comprising the first diol and the extractant to distillation in a third distillation to provide a top stream comprising the first diol in high purity, wherein the extractant is selected from the group of C3 to C6 sugar alcohols and mixtures thereof.

DETAILED DESCRIPTION OF THE INVENTION

Figure 1:
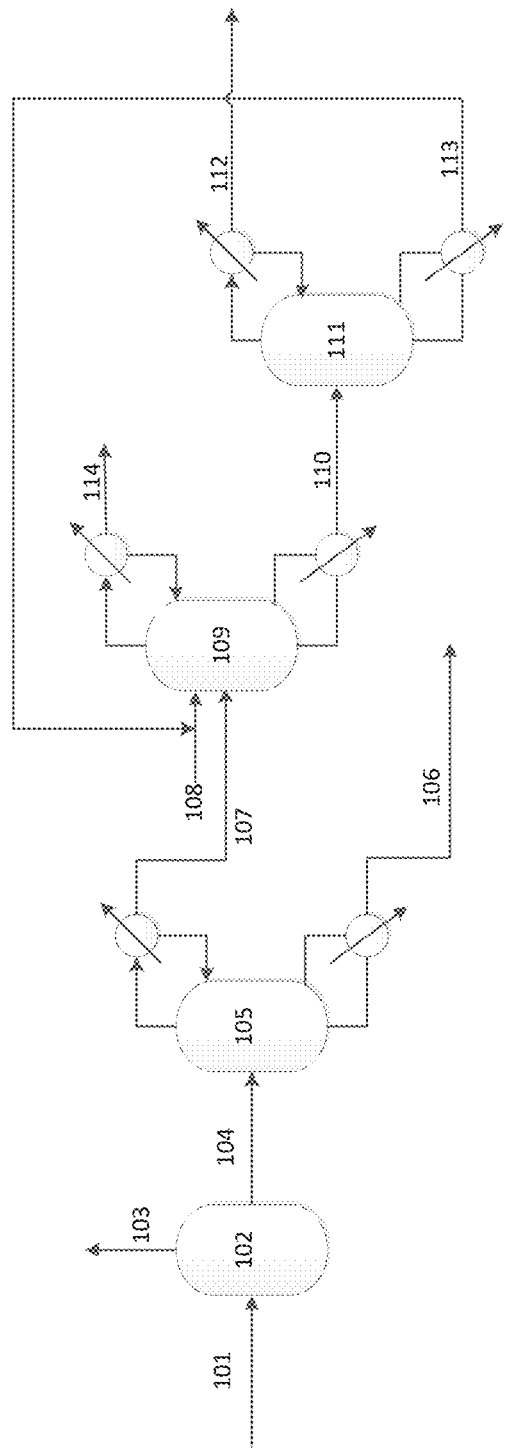
FIGS. 1 and 2 are schematic diagrams of exemplary, but non-limiting, embodiments of the process for the separation of glycols as described herein.

The present inventors have determined a new method for the production of a high purity diol from a product stream. Preferably, said product stream is derived from a saccharide hydrogenolysis process. Such a product stream from a process for the hydrogenolysis of a saccharide-containing feedstock comprises certain desirable diols as well as by-products comprising diols and other materials.

The product stream comprises two or more C2 to C7 diols. Preferably, said two or more C2 to C7 diols, including said first diol, are selected from the group consisting of C2 to C7 glycols. The term glycol as used herein is given its usual meaning, i.e. a diol in which the two hydroxyl groups are present on vicinal carbon atoms. Preferably, the first diol is monoethylene glycol (MEG) and the product stream comprises MEG and 1,2-butanediol (1,2-BDO), or the first diol is monopropylene glycol (MPG) and the product stream comprises MPG and 2,3-pentanediol. Most preferably, the first diol is monoethylene glycol (MEG) and the product stream comprises MEG and 1,2-butanediol (1,2-BDO)

In this particularly preferred embodiment, the process for the production of a high purity first diol is a process for the production of high purity MEG from a product stream comprising a mixture of MEG and 1,2-BDO, said process comprising the steps of:

(i) subjecting the product stream to distillation in a first distillation column to provide a bottoms stream comprising high boiling by-products and a top stream comprising a mixture of MEG and 1,2-BDO;

(ii) providing said mixture comprising MEG and 1,2-BDO as a feed to a second distillation column;

(iii) providing a feed comprising an extractant to the second distillation column above the mixture comprising MEG and 1,2-BDO;

(iv) operating the second distillation column at a temperature in the range of from 50 to 250° C. and a pressure in the range of from 0.1 to 400 kPa;

(v) removing a stream comprising MEG and the extractant as a bottoms stream from the second distillation column; and (vi) subjecting the stream comprising MEG and the extractant to distillation in a third distillation column to provide a top stream comprising MEG in high purity, wherein the extractant is selected from the group of C3 to C6 sugar alcohols and mixtures thereof.

In a preferred embodiment the product stream is, or is derived from, a reaction product stream from a process for the hydrogenolysis of a saccharide-containing feedstock, which as well as diols will also contain a solvent. In this embodiment, it is preferred that prior to subjecting the product stream to distillation in the first distillation column, the product stream is subjected to solvent removal, e.g. by distillation, in order to provide a solvent-lean product stream.

Typically, the reaction product stream from a process for the hydrogenolysis of a saccharide-containing feedstock comprises, as diols, at least MEG, MPG and 1,2-BDO. Other diols, such as 2,3-BDO, pentanediols, hexanediols and heptanediols may also be present. These diols are typically present at a concentration in the range of from 0.1 to 30 wt % of the overall reaction product stream.

In such a reaction product stream, MEG is suitably present as at least 10 wt %, preferably as at least 30 wt % of the non-solvent fraction of the stream. MEG is suitably present as at most 95 wt %, preferably as at most 90 wt %, most preferably as at most 80 wt % of the non-solvent fraction of the stream.

In such a reaction product stream, MPG is suitably present as at least 2 wt %, preferably as at least 4 wt % of the non-solvent fraction of the stream. MPG is suitably present as at most 45 wt %, preferably as at most 20 wt % of the non-solvent fraction of the stream.

In such a reaction product stream, 1,2-BDO is typically present as at least 1 wt %, generally as at least 4 wt % of the non-solvent fraction of the stream. 1,2-BDO is suitably present as at most 20 wt %, preferably as at most 8 wt % of the non-solvent fraction of the stream.

The hydrogenolysis reaction is carried out in the presence of a solvent. Therefore, the reaction product stream will also contain said solvent. The solvent may be water or a $C_1$ to $C_6$ alcohol or polyalcohol (including sugar alcohols) or mixtures thereof. Preferred $C_1$ to $C_6$ alcohols include methanol, ethanol, 1-propanol and iso-propanol. Polyalcohols of use include glycols, particularly products of the hydrogenation/hydrogenolysis reaction, glycerol, erythritol, threitol, sorbitol and mixtures thereof. Preferably, the solvent comprises water.

As well as the C2 to C7 diols and the solvent, the reaction product streams from hydrogenolysis reactions of saccharides may comprise oxygenates, hydrocarbons, catalyst, degradation products, and gases in any composition. The variety of compounds and their concentration depend on the saccharide-containing feedstock and the various hydrogenation and hydrogenolysis conversion conditions, including catalysts, reaction conditions such as temperature, pressure and saccharide concentration. However, suitably the hydrogenolysis reactions have gone to completion and the aqueous stream contains less than 5 wt %, preferably less than 2 wt %, more preferably less than 1 wt %, even more preferably less than 0.5 wt %, most preferably substantially no saccharides when considered as a weight percentage of the overall stream. If the solvent used comprises water or a $C_1$ to $C_6$ alcohol typically, the reaction product stream also contains less than 5 wt %, preferably less than 2 wt %, more preferably less than 1 wt %, even more preferably less than 0.5 wt %, most preferably substantially no glycerol, when considered as a weight percentage of the overall stream.

In the process of the present invention, solvent, for example water, may be removed from the product stream, e.g. by distillation, prior to subjecting the product stream to distillation in the first distillation column. In this embodiment, the solvent removal may be carried out in a single distillation column. Preferably, it is carried out over a number of distillation steps, for example by multi-effect evaporation or a combination of multi-effect evaporation and solvent removal (e.g. dehydration) by distillation.

In this embodiment, the solvent present in the reactor is removed to provide a solvent-lean product stream. The term 'solvent-lean' used herein refers to the fact that the product stream is essentially solvent free. In practice, a small amount of solvent may be present in the solvent-lean product stream within the scope of the invention. If the solvent comprises water or a $C_1$ to $C_6$ alcohol, then preferably no more than 1000 ppmw, more preferably no more than 400 ppmw, even more preferably no more than 200 ppmw, most preferably no more than 100 ppmw of solvent is present in the solvent-free product stream. If a polyalcohol, such as a sugar alcohol is used as the solvent, a higher amount of the solvent may be tolerated in the 'solvent-lean' product stream.

Other steps, such as removal of light ends or filtration off of a heterogeneous catalyst, may also be applied to the product stream upstream or downstream of the step of removing the solvent. The use of such steps will depend on the conditions and/or reaction mixture in the saccharide hydrogenolysis process.

The product stream, preferably the solvent-lean product stream, is then subjected to distillation in a first distillation column to provide a bottoms stream comprising high boiling by-products, referred to herein as 'heavies', and a top stream comprising a mixture comprising the two or more C2 to C7 diols.

In one embodiment, preferably, said top stream comprises at least a mixture comprising MEG and 1,2-BDO. Other materials, such as MPG and other light glycols may be present in the mixture comprising MEG and 1,2-BDO. In this embodiment, the mixture comprising MEG and 1,2-BDO preferably has a weight ratio of MEG:1,2-BDO of at least 5:1. More preferably the weight ratio of MEG:1,2-BDO is at least 25:1. Most preferably the weight ratio of MEG:1,2-BDO is at least 150:1.

In another embodiment, preferably, said top stream comprises at least a mixture comprising MPG and 2,3-pentanediol. Other materials, such as light glycols may be present in the mixture comprising MPG and 2,3-pentanediol. In this embodiment, the mixture comprising MPG and 2,3-pentanediol preferably has a weight ratio of MPG:2,3-pentanediol of at least 5:1. More preferably the weight ratio of MPG:2,3-pentanediol is at least 25:1. Most preferably the weight ratio of MPG:2,3-pentanediol is at least 150:1.

The mixture comprising the two or more C2 to C7 diols is provided as a feed to a second distillation column. The second distillation column may be any suitable sort of column known in the art and may be equipped with trays or structured or unstructured packing. The number of theoretical stages may vary in the range of from 3 to 140 and may easily be determined by the skilled person on the basis of simple economic optimization experiments.

A feed comprising an extractant is provided to the second distillation column above the point at which the feed of the mixture comprising the two or more C2 to C7 diols is provided. Preferably, the feed comprising an extractant is provided at the top of or a few stages below the top of the second distillation column.

The extractant is selected from the group of C3 to C6 sugar alcohols and mixtures thereof. Sugar alcohols have the general formula $HOCH_2(CHOH)_nCH_2OH$. Suitable sugar alcohols include glycerol, erythritol, threitol, arabitol, xylitol, ribitol, mannitol, sorbitol, galacticol and iditol. Although some of these sugar alcohols may be solid at room temperature, pressures and compositions for suitable extractant mixtures, they can be used as liquids at suitable temperatures and pressures in the process of the invention. In a preferred embodiment of the present invention, the extractant comprises glycerol.

As well as the extractant, this stream may also comprise certain heavies, such as other poly-alcohols, especially other sugar alcohols, from a recycle stream in the process. One example of a suitable recycle stream is the bottoms stream comprising high boiling by-products provided in step (ii) of the instant process. Such high boiling by-products will include C3-C6 sugar alcohols. Preferably, at least a portion of said bottoms stream may be used as at least a portion of the extractant, more preferably after distillation to remove the heaviest portion of said bottoms stream.

Preferably, the extractant is added in an amount such that the weight ratio of the feed comprising extractant to the mixture comprising the two or more C2 to C7 diols is at least 0.05:1, more preferably at least 0.1:1, even more preferably at least 0.25:1, based on the overall weight of the feed/mixture. Preferably, the weight ratio of the feed comprising the extractant to the first mixture comprising the two or more C2-C7 diols is at most 10:1, more preferably at most 5:1, even more preferably 2:1, more preferably at most 1.5:1, based on the overall weight of the feed/mixture.

The distillation in the second distillation column is carried out at a temperature in the range of from 50 to 250° C., preferably of from 100 to 200° C. and at a pressure of at least 0.1 kPa. Generally, a pressure of at least 1 kPa is preferred for economic reasons, with a pressure of at least 5 kPa more preferred for the same reasons. The pressure is at most 400 kPa, preferably at most 200 kPa, more preferably at most 120 kPa. It will be clear to the skilled person to vary the temperature and pressure in relation to each other in order to achieve suitable conditions.

A secondary stream comprising one or more C2 to C7 diols is removed from the second distillation column above the point at which the feed comprising an extractant is provided to the second distillation column. In the separation of MEG and 1,2-BDO, this stream would comprise 1,2-BDO; and in the separation of MPG and 2,3-pentanediol, this stream would comprise 2,3-pentanediol. Preferably, the secondary stream is removed from the second distillation column as a condensed overheads stream.

This stream may contain other diols, such as MPG, 2,3-BDO, pentanediols, hexanediols and heptanediols. Preferably, this stream is subjected to one or more fractional distillation steps in order to produce desired products as pure product streams.

A stream comprising the first diol, preferably MEG or MPG, and the extractant is removed from the second distillation column as a bottoms stream.

In the preferred embodiment in which the first diol is MEG, suitably, the diols content of this bottoms stream, comprises at least 95 wt % MEG, preferably at least 98 wt % MEG, more preferably at least 99 wt % MEG, even more preferably at least 99.5 wt % MEG, most preferably at least 99.9 wt % MEG.

This stream is then subjected to a further distillation step in a third distillation column in which the first diol, preferably MEG, is distilled off to provide a high purity first diol stream. This distillation is carried out at the same or lower pressure than in the extractive distillation step (in the second distillation column) in order to restrict the temperature in the reboiler and avoid or minimize potential product degradation.

High purity diol as used herein refers to a diol of at least 99 wt % purity, preferably at least 99.5 wt %, more preferably at least 99.6 wt % purity, most preferably at least 99.9 wt % purity.

Preferably, in the embodiment wherein the first diol is MEG, the high purity MEG is suitable for use as fibre grade MEG.

The bottoms stream from this distillation comprises a used extractant stream.

At least a portion of the used extractant stream may then be recycled to the second distillation column as at least a portion of the feed comprising an extractant. Any heavies left that had been present in the first mixture comprising MEG and 1,2-BDO may also be present in the extractant stream to be recycled. If the mixture comprising two or more C2 to C7 diols and a solvent is derived from the reaction product stream from a process for the hydrogenolysis of a saccharide-containing feedstock, such heavies are likely to be sugar alcohol like in their structure, boiling point and other physical properties and may be recycled with the rest of the extractant stream.

A portion of this used extractant stream may be removed as a bleed in order to prevent a build-up of heavies. In this embodiment, fresh extractant will need to be provided to the second distillation column to make up the required amount of extractant. This fresh extractant should be provided to the second distillation column at the same height or above the used extractant stream.

Optionally, at least a portion of this recycle stream may be subjected to further processing steps to further increase its purity. Optionally, the first diol, preferably MEG, stream may be subjected to further processing steps to further increase its purity or remove trace compounds that could affect the quality of the final product.

The present invention has a number of advantages over prior art processes, wherein problems are encountered with close-boiling and azeotrope-forming by-products. After reaction-solvent removal, the separation of diols is based on a two-step process. Firstly, heavy (high-boiling) by-products are removed by distillation in a first distillation column. Then, in a second distillation column, one or more sugar alcohols is used as extractant for the selective extractive distillation of the first diol. The strong interaction between the sugar alcohols and the first diol breaks any azeotrope and affects the volatility of the diols present, allowing them to be separated. A simple distillation of the first diol as overhead product from the extractant in a third distillation column results in a high purity first diol stream, for example high purity MEG suitable for use as fibre grade MEG either immediately or after removal of trace compounds.

Optionally, a finishing section may be added to the top of this third distillation column in order to remove any type of light impurities/light degradation products formed at the separation process. This section would be above the point at which the high purity first diol stream is removed.

The combination of a heavies removal (first distillation) column followed by extractive distillation (in the second distillation column) has been termed 'orthogonal separation'. This robust process allows diols to be separated from the by-products of a saccharide hydrogenolysis reaction in high purity and with high recovery of said diols. Suitably at least 90 wt %, preferably at least 95 wt %, more preferably at least 98 wt % and most preferably at least 99.9 wt % of the first diol formed in the hydrogenolysis reaction is recovered.

DETAILED DESCRIPTION OF THE DRAWINGS

The invention will now be further illustrated with reference to the non-limiting embodiments shown in the drawings. In the drawings, the first numeral of each reference number refers to the Figure number, e.g. 1XX for FIGS. 1 and 2XX for FIG. 2. The remaining figures relate to the individual features within the Figures. The same number is used to refer to the same feature in each Figure. Therefore, 107 refers to the same feature in FIG. 1 as 207 refers to in FIG. 2.

In this description, the separation of high purity MEG from a mixture comprising MEG and 1,2-BDO from a saccharide hydrogenolysis process is described. The same system could be used to separate other mixtures such as MPG and 2,3-pentanediol.

In FIG. 1, a product stream 101 from a saccharide hydrogenolysis process, is subjected to one or more distillation processes 102 to remove solvent 103, suitably water. Suitable steps to remove light compounds may also have been applied to this stream. The solvent-free stream 104 is then supplied to a first distillation column 105 where it undergoes distillation to remove high boiling products 106. The resulting stream 107 comprising a mixture comprising MEG and 1,2-BDO is then supplied as a feed to a second distillation column 109. A feed comprising an extractant 108 is provided to the second distillation column 109 above the mixture comprising MEG and 1,2-BDO. A stream comprising MEG and the extractant 110 is removed from the bottom of the second distillation column 109 and supplied to a third distillation column 111, wherein a top stream comprising high purity MEG 112 is obtained. The bottoms stream 113 from this distillation can be recycled to form at least a portion of the feed comprising an extractant 108. An overheads stream 114 from the third distillation column 109 will comprise 1,2-BDO and typically, other diols.

Fresh extractant may be added to the feed comprising an extractant 108, as required.

The 'orthogonal separation' concept of this application is illustrated by the combination of the three columns 105, 109 and 111.

Figure 2:
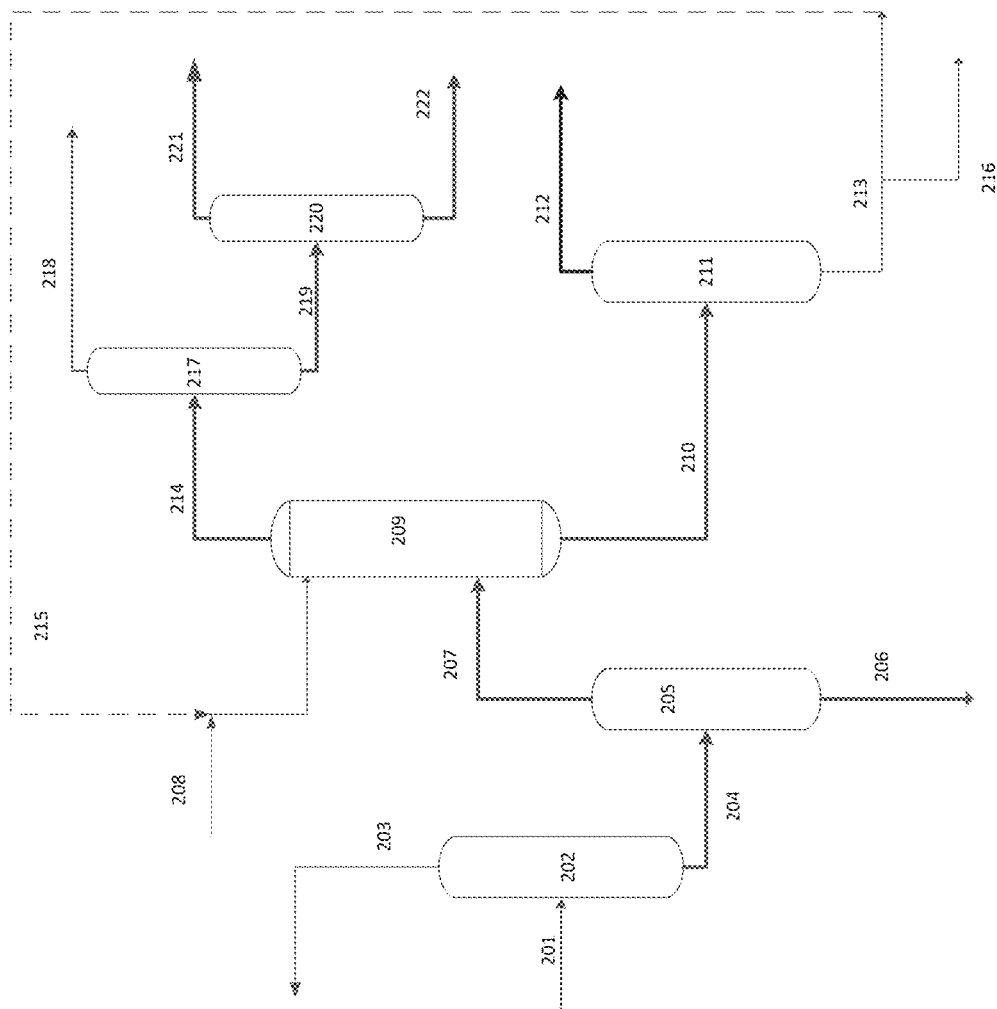

A further illustration of the invention is shown in FIG. 2. In this embodiment, the overheads stream 214 is further purified in a first fractional distillation column 217, to provide an overheads stream 218 of 2,3-BDO. The bottoms stream 219 from the first fractional distillation column 217 may then be provided to a second fractional distillation column 220 to provide a high purity MPG stream 221 and a stream comprising residual glycols, such as 1,2-BDO, 1,2-pentanediol, etc.

An extractant bleed stream 216 is also illustrated in FIG. 2. The remainder of the bottoms stream 213 is recycled to provide at least a portion 215 of the feed comprising an extractant 208. Potential heat integrations may be used to increase the energy efficiency of the system, for example recovering the heat from the extractant recycle 215 to use it on a side reboiler for the extractive distillation column 209.

EXAMPLES

The invention will be further illustrated by the following, non-limiting examples.

Example 1

Experimental basic data measurements were taken for the vapour-liquid-equilibrium for the ternary system comprising MEG, 12-BDO and Glycerol. Data points were measured at low/vacuum pressures and different compositions.

Aspen Plus software was used to model the process as shown in FIG. 1. A thermodynamic package was used. Said package resulted from fitting of the experimental basic data (VLE) measured for the mixtures considered.

Examples were then generated from Aspen Plus using glycerol as the extractant (entrainer) and feed mixtures with different MEG/1,2-BDO weight ratios and glycerol/MEG mixture weight ratios.

In each example, the MEG mixture is fed to the second (extractive) distillation column 109 at about the middle of its height. The glycerol feed 108 location is at the upper part of the column (first stages). The results for the second (extractive) distillation column 109 are shown in Tables 1 to 4, below.

The results for the third distillation (solvent recovery) column 111 that provides final MEG 99.9% wt. purity are shown in Table 7. This last MEG purification step comprises the distillation of MEG from the solvent in a rectification column with low number of stages and low reflux ratio, thanks to the high relative volatility of MEG compared to the extractive solvents used.

TABLE 1

MEG/1,2-BDO Ratio of 31; Glycerol/MEG Mixture Weight Ratio of 6.5; 99.5% MEG Recovery and 99.9% 12-BDO Recovery

|  | Feed MEG mixture | Feed Glycerol | Top | Bottom |
|---|---|---|---|---|
| Temperature | 130° C. | 170° C. | 126° C. | 190° C. |
| Pressure | 1.2 Bar | 1.2 Bar | 0.1 Bar | 0.13 bar |
| Component | Wt. % | Wt. % | Wt. % | Wt. % |
| Glycerol | 0 | ≈100 | ≈0 | 88.2 |
| MEG | 87.4 | ≈0 | 3.4 | 11.8 |
| MPG | 9 | 0 | 69.2 | ≈0 |
| 1,2-BDO | 2.8 | 0 | 21.6 | ≈0 |
| 2,3-BDO | 0.45 | 0 | 3.5 | ≈0 |
| 1,2-PDO | 0.11 | 0 | 0.7 | 0.0025 |
| 2,3-PDO | 0.23 | 0 | 1.73 | ≈0 |
| 1,2-HDO | 0.01 | 0 | ≈0 | 0.0015 |

PDO and HDO make reference to pentanediol and hexanediol glycols, respectively.

TABLE 2

MEG/1,2-BDO Ratio of 16; Glycerol/MEG Mixture Weight Ratio of 6.5; 99.5% MEG Recovery and 99.9% 12-BDO Recovery

|  | Feed MEG mixture | Feed Glycerol | Top | Bottom |
|---|---|---|---|---|
| Temperature | 130° C. | 170° C. | 127° C. | 191° C. |
| Pressure | 1.2 Bar | 1.2 Bar | 0.1 Bar | 0.13 bar |
| Component | Wt. % | Wt. % | Wt. % | Wt. % |
| Glycerol | 0 | ≈100 | ≈0 | 88.5 |
| MEG | 85.0 | ≈0 | 2.8 | 11.5 |
| MPG | 8.8 | 0 | 56.9 | ≈0 |
| 1,2-BDO | 5.5 | 0 | 35.5 | ≈0 |
| 2,3-BDO | 4.4 | 0 | 2.8 | ≈0 |
| 1,2-PDO | 0.11 | 0 | 0.6 | 0.0029 |
| 2,3-PDO | 0.23 | 0 | 1.4 | ≈0 |
| 1,2-HDO | 0.01 | 0 | ≈0 | 0.0015 |

TABLE 3

MEG/1,2-BDO Ratio of 31; Glycerol/MEG Mixture Weight Ratio of 5; 95% MEG Recovery and 99.9% 12-BDO Recovery

|  | Feed MEG mixture | Feed Glycerol | Top | Bottom |
|---|---|---|---|---|
| Temperature | 130° C. | 170° C. | 128° C. | 188° C. |
| Pressure | 1.2 Bar | 1.2 Bar | 0.1 Bar | 0.13 bar |

TABLE 3-continued

MEG/1,2-BDO Ratio of 31; Glycerol/MEG Mixture Weight Ratio of 5; 95% MEG Recovery and 99.9% 12-BDO Recovery

|  | Feed MEG mixture | Feed Glycerol | Top | Bottom |
|---|---|---|---|---|
| Component | Wt. % | Wt. % | Wt. % | Wt. % |
| Glycerol | 0 | ≈100 | ≈0 | 85.6 |
| MEG | 87.4 | ≈0 | 25.6 | 14.25 |
| MPG | 9 | 0 | 53.1 | ≈0 |
| 1,2-BDO | 2.8 | 0 | 16.6 | ≈0 |
| 2,3-BDO | 0.45 | 0 | 2.7 | ≈0 |
| 1,2-PDO | 0.11 | 0 | 0.6 | 0.0029 |
| 2,3-PDO | 0.23 | 0 | 1.3 | ≈0 |
| 1,2-HDO | 0.01 | 0 | ≈0 | 0.002 |

TABLE 4

MEG/1,2-BDO Ratio of 52; Glycerol/MEG Mixture Weight Ratio of 2; 95% MEG Recovery and 99.5% 12-BDO Recovery

|  | Feed MEG mixture | Feed Glycerol | Top | Bottom |
|---|---|---|---|---|
| Temperature | 130° C. | 170° C. | 127° C. | 166° C. |
| Pressure | 1.2 Bar | 1.2 Bar | 0.1 Bar | 0.13 bar |
| Component | Wt. % | Wt. % | Wt. % | Wt. % |
| Glycerol | 0 | ≈100 | ≈0 | 61.4 |
| MEG | 88.4 | ≈0 | 27.8 | 38.6 |
| MPG | 9.1 | 0 | 57.2 | ≈0 |
| 1,2-BDO | 1.7 | 0 | 10.7 | ≈0 |
| 2,3-BDO | 0.45 | 0 | 2.9 | ≈0 |
| 1,2-PDO | 0.06 | 0 | 0.0005 | 0.026 |
| 2,3-PDO | 0.23 | 0 | 1.4 | ≈0 |
| 1,2-HDO | 0.01 | 0 | ≈0 | 0.0052 |

These examples show the separation performance for mixtures of MEG, MPG, 12-BDO, 1,2-BDO, 1,2-PDO, 2,3-PDO and 1,2-HDO. MEG/12-BDO ratios of 16, 31 and 52 have been used. Simulations for Glycerol/MEG weight ratios of 6.5, 5 and 2 have been conducted, rendering MEG (bottom stream) and 1,2-BDO (top stream) recoveries ranging from 95% to 99.9%.

The examples demonstrate the production of a bottoms stream containing extractant (glycerol), MEG and minor glycol impurities, which after distillation of MEG off the extractant would result in an MEG stream of at least 99.9 wt % purity.

Example 2

Aspen Plus software was used to model the process as shown in FIG. 1. A thermodynamic package was used. Said package resulted from fitting of experimental basic data of the vapour pressure curves for the individual components and the vapour-liquid equilibrium (VLE) measured for mixtures of those components.

Examples were then generated from Aspen Plus using glycerol as the extractant (entrainer) and feed mixtures with different MPG/other glycols weight ratios and glycerol/MPG mixture weight ratios, to exemplify the separation and purification of a glycol with 3 carbon atoms, in this case MPG. For this application, the separation of MPG from close boilers as 2,3-Pentanediol species is a challenge since those glycols form close-boiling point azeotropes when compared to the pure components.

In each case, the MPG mixture is fed first to a first distillation column 105 in which the heavy components are removed. The results of this distillation are exemplified in Table 5. Then, the resulting top product is fed to the extractive distillation (second distillation column). In each example, the MPG mixture is fed to the second (extractive) distillation column 109 at about the middle of its height. The glycerol feed 108 location is at the upper part of the column (first stages). The results for the second (extractive) distillation column 109 are shown in Table 6.

The results for the third distillation (solvent recovery) column 111 that provides final MPG high-purity product are shown in Table 7. This MPG last purification step comprises the distillation of MPG from the solvent in a rectification (third distillation) column with low number of stages and low reflux ratio, making use of the high relative volatility of the glycol (MPG) compared to the extractive solvents used.

The examples in the following tables use: MPG initial concentration of 71.8% wt; Glycerol/MPG mixture weight ratio of 8.6 (mass) towards second (extractive) distillation column; Overall MPG recovery of 98%. MPG recovery on the extractive distillation of 99% (bottom) with 98% 23-PDO recovery (top). Final MPG product purity of 99.96% wt is then achieved in column 111.

TABLE 5

Results for the first distillation column 105

|  | Feed MPG mixture | Top | Bottom |
|---|---|---|---|
| Temperature | 130.0° C. | 141.1° C. | 160.8° C. |
| Pressure | 1.2 Bar | 0.2 Bar | 0.13 bar |
| Component | Wt. % | Wt. % | Wt. % |
| Glycerol | 2.7 | 0.0 | 8.9 |
| Sorbitol | 2.7 | 0.0 | 8.9 |
| Isosorbitol | 2.7 | 0.0 | 8.9 |
| MEG | 3.6 | 0.0 | 12.0 |
| MPG | 71.8 | 97.5 | 12.0 |
| 1,2-BDO | 13.5 | 0.0 | 44.7 |
| 2,3-BDO | 0.9 | 1.3 | 0.0 |
| 1,2-PDO | 0.4 | 0.0 | 1.5 |
| 2,3-PDO | 0.9 | 1.2 | 0.1 |
| 1,2-HDO | 0.4 | 0.0 | 1.5 |
| 1,2-HHDO | 0.4 | 0.0 | 1.5 |

PDO, HDO and HHDO make reference to pentanediol, hexanediol and heptanediols glycols, respectively.

TABLE 6

Results for the second distillation column 109

|  | Feed MPG mixture | Feed Glycerol | Top | Bottom |
|---|---|---|---|---|
| Temperature | 141° C. | 170° C. | 107.6° C. | 170.5° C. |
| Pressure | 1.2 Bar | 1.2 Bar | 0.05 Bar | 0.10 bar |
| Component | Wt. % | Wt. % | Wt. % | Wt. % |
| Glycerol | 0.00 | ≈100 | 2.2 | 89.9 |
| Sorbitol | 0.00 | 0 | 0.0 | 0.0 |
| Isosorbitol | 0.00 | 0 | 0.0 | 0.0 |
| MEG | 0.00 | 0 | 0.0 | 0.0 |
| MPG | 97.50 | 0 | 28.1 | 10.1 |
| 1,2-BDO | 0.00 | 0 | 0.0 | 0.0 |
| 2,3-BDO | 1.30 | 0 | 35.4 | 0.0 |
| 1,2-PDO | 0.00 | 0 | 0.0 | 0.0 |
| 2,3-PDO | 1.20 | 0 | 34.3 | 0.0 |
| 1,2-HDO | 0.00 | 0 | 0.0 | 0.0 |
| 1,2-HHDO | 0.00 | 0 | 0.0 | 0.0 |

TABLE 7

Results for the third distillation column 111

|  | Feed MPG mixture | Top | Bottom |
|---|---|---|---|
| Temperature | 170° C. | 110° C. | 200° C. |
| Pressure | 1.2 Bar | 0.2 Bar | 0.13 bar |
| Component | Wt. % | Wt. % | Wt. % |
| Glycerol | 89.90 | ≈0 | 100.0 |
| Sorbitol | 0.00 | 0.0 | 0.0 |
| Isosorbitol | 0.00 | 0.0 | 0.0 |
| MEG | 0.00 | 0.0 | 0.0 |
| MPG | 10.10 | 99.96 | 0.0 |
| 1,2-BDO | 0.00 | 0.01 | 0.0 |
| 2,3-BDO | 0.00 | 0.03 | 0.0 |
| 1,2-PDO | 0.00 | 0.0 | 0.0 |
| 2,3-PDO | 0.00 | 0.0 | 0.0 |
| 1,2-HDO | 0.00 | 0.0 | 0.0 |
| 1,2-HHDO | 0.00 | 0.0 | 0.0 |

That which is claimed is:

1. A process for the production of a high purity first diol, selected from the group consisting of C2 to C7 diols from a product stream comprising two or more C2 to C7 diols, said process comprising the steps of:
   (i) subjecting the product stream to distillation in a first distillation column to provide a bottoms stream comprising high boiling by-products and a top stream comprising a mixture comprising the two or more C2 to C7 diols;
   (ii) providing said mixture comprising the two or more C2 to C7 diols as a feed to a second distillation column;
   (iii) providing a feed comprising an extractant to the second distillation column above the mixture comprising the two or more C2 to C7 diols;
   (iv) operating the second distillation column at a temperature in the range of from 50 to 250° C. and a pressure in the range of from 0.1 to 400 kPa;
   (v) removing a stream comprising the first diol and the extractant as a bottoms stream from the second distillation column; and
   (vi) subjecting the stream comprising the first diol and the extractant to distillation in a third distillation column to provide a top stream comprising the first diol in high purity, wherein the extractant is selected from the group of C3 to C6 sugar alcohols and mixtures thereof.

2. The process according to claim 1, wherein the first diol is MEG and the product stream comprises at least MEG and 1,2-BDO.

3. The process according to claim 2, wherein the first diol is MPG and the product stream comprises at least MPG and 2,3-pentanediol.

4. The process according to claim 1, wherein the product stream is, or is derived from, a product stream of a saccharide hydrogenolysis process.

5. The process according to claim 4, wherein said product stream comprises at least MEG and 1,2-BDO and a solvent and prior to step (i) the solvent is removed from the product stream to provide a solvent-lean product stream.

6. The process according to claim 1, wherein a bottoms stream comprising a used extractant stream is also obtained in step (vi).

7. The process according to claim 6, wherein at least a portion of the bottoms stream comprising the used extractant is then recycled to the second distillation column as at least a portion of the feed comprising an extractant.

8. The process according to claim 1, wherein the feed comprising the extractant is provided at the top of or a few trays below the top of the second distillation column.

9. The process according to claim 6, wherein a portion of the used extractant stream is removed as a bleed stream.

10. The process according to claim 9, wherein fresh extractant is provided to the second distillation column, at the same height or above the used extractant stream, to make up the required amount of extractant.

11. The process according to claim 2, wherein the first mixture comprising MEG and 1,2-BDO has a weight ratio of MEG:1,2-BDO of at least 5:1.

12. The process according to claim 1, wherein the extractant is added in an amount such that the weight ratio of the feed comprising an extractant to the feed comprising the mixture comprising the two or more C2 to C7 diols is at least 0.25:1 and at most 10:1 based on the overall weight of the feed/mixture.

13. The process according to claim 1, wherein glycols content of the stream comprising the first diol and the extractant, comprises at least 99.9wt % of the first diol.

14. The process according to claim 1, wherein a finishing section is added to the top of the third distillation column above the point at which the high purity first diol stream is obtained, in order to remove any type of light impurities/light degradation products formed in the separation process.

* * * * *